United States Patent [19]

Kojima

[11] Patent Number: 5,000,188

[45] Date of Patent: Mar. 19, 1991

[54] PHYSIOLOGICAL AGE MEASURING APPARATUS

[75] Inventor: Osamu Kojima, Tajimi, Japan

[73] Assignee: Colin electronics Co., Ltd., Japan

[21] Appl. No.: 442,058

[22] Filed: Nov. 28, 1989

[30] Foreign Application Priority Data

Jun. 13, 1989 [JP] Japan ............................... 1-151105

[51] Int. Cl.$^5$ ............................................. A61B 5/02
[52] U.S. Cl. .................................................. 128/687
[58] Field of Search ............... 128/687, 688, 696, 672, 128/702

[56] References Cited

U.S. PATENT DOCUMENTS

| 4,572,199 | 2/1986 | LaCourse ........................... 128/688 |
| 4,721,114 | 6/1988 | DuFault et al. .................... 128/696 |
| 4,742,458 | 5/1988 | Nathaus et al. .................... 128/702 |
| 4,777,959 | 10/1988 | Wallach et al. .................... 128/672 |

*Primary Examiner*—Francis Jaworski
*Assistant Examiner*—George Manuel
*Attorney, Agent, or Firm*—Oliff & Berridge

[57] ABSTRACT

An apparatus for measuring a physiological age of a subject, including a sampling device for sampling a waveform of pulse wave produced from an arterial vessel of a subject, a storing device for storing a plurality of reference waveform models corresponding to a plurality of physiological age groups, respectively, and a determining device for selecting one of the plurality of reference waveform models which is most similar to the sampled waveform of the subject, and determining a physiological age of the subject based on the age group corresponding to the selected reference waveform model.

6 Claims, 2 Drawing Sheets

PHYSIOLOGICAL AGE MEASURING APPARATUS

BACKGROUND OF THE INVENTION

1. Field of the Invention

The present invention relates to an apparatus for measuring a physiological age of a subject based on pulse wave produced from an arterial vessel of the subject.

2. Discussion of the Prior Art

It has been proposed to measure a degree of sclerosis of arterial vessel of a subject based on pulse wave produced from the arterial vessel. Such an apparatus is disclosed in Japanese Patent Application laid open under Publication No. 61-119252 on June 6, 1986, the assignee of which is the assignee of the present U.S. patent application. The disclosed apparatus selects one of a plurality of reference waveform patterns which correspond to a plurality of respective degrees of sclerosis of arterial vessel, such that the selected reference waveform pattern shows the highest correlation with the sampled waveform of pulse wave of the subject, and determines the degree of sclerosis corresponding to the selected waveform pattern, as a degree of sclerosis of the arterial vessel of the subject. Thus, this apparatus permits measurement of an arteriosclerosis degree of a subject, irrespective of whether experience of the operator is rich or poor.

However, the above-indicated apparatus is not capable of measuring a physiological age of a subject, and accordingly is not capable of permitting calculation of a difference between the measured physiological age and a real age of the subject.

SUMMARY OF THE INVENTION

It is therefore an object of the present invention to provide an apparatus for measuring a physiological age of a subject based on the pulse wave produced from an arterial vessel of a subject.

The Inventor has found that the waveform of pulse wave produced from an arterial vessel of a person, reflects his or her physiological age, and that the waveform is varied primarily by variation in blood output of the heart, and variation in degree of arteriosclerosis. In other words, it is possible to measure a physiological age of a subject based on the waveform of pulse wave produced from an arterial vessel of the subject, and calculate a difference between the measured physiological age and a real age of the subject. Thus, it is identified whether or not the subject is physiologically young or old, in particular what degree of arteriosclerosis the subject suffers from.

According to the principle of the present invention, there is provided an apparatus for measuring a physiological age of a subject, comprising sampling means for sampling a waveform of pulse wave produced from an arterial vessel of a subject, storing means for storing a plurality of reference waveform models corresponding to a plurality of physiological age groups, respectively, and determining means for selecting one of the plurality of reference waveform models which is most similar to the sampled waveform of the subject, and determining a physiological age of the subject based on the age group corresponding to the selected reference waveform model.

In the physiological age measuring apparatus constructed as described above, one waveform model is selected from the plurality of reference waveform models corresponding to the plurality of physiological age groups or classes, such that the selected waveform model is the most similar to the sampled waveform of the pulse wave detected from the arterial vessel of a subject, and a physiological age of the subject is determined based on the age group corresponding to the selected waveform model. Thus, the present apparatus is capable of measuring a physiological age of a subject and permits calculation of a difference between the measured physiological age and a real age of the subject, making it possible to determine what degree the subject is physiologically young or old.

According to a feature of the present invention, the sampling means comprises a pulse wave sensor which is pressed against the arterial vessel via a body surface over the arterial vessel so as to detect the pulse wave transmitted thereto from the arterial vessel via the body surface.

According to another feature of the present invention, the plurality of physiological age groups consist of infant, young, middle and old age groups. Alternatively, the plurality of physiological age groups may consist of ten age groups like 0-9 year-old group, 10-19, 20-29 and so on.

According to yet another feature of the present invention, the apparatus further comprises display means for displaying the determined physiological age.

According to a further feature of the present invention, the determining means selects one of the plurality of reference waveform models which has a greatest correlation coefficient with respect to the sampled waveform of the subject.

BRIEF DESCRIPTION OF THE DRAWINGS

The above and optional objects, features and advantages of the present invention will be better understood by reading the following detailed description of the presently preferred embodiment of the invention when considered in conjunction with the accompanying drawings, in which.

DETAILED DESCRIPTION OF THE PREFERRED EMBODIMENT

Figure 1:
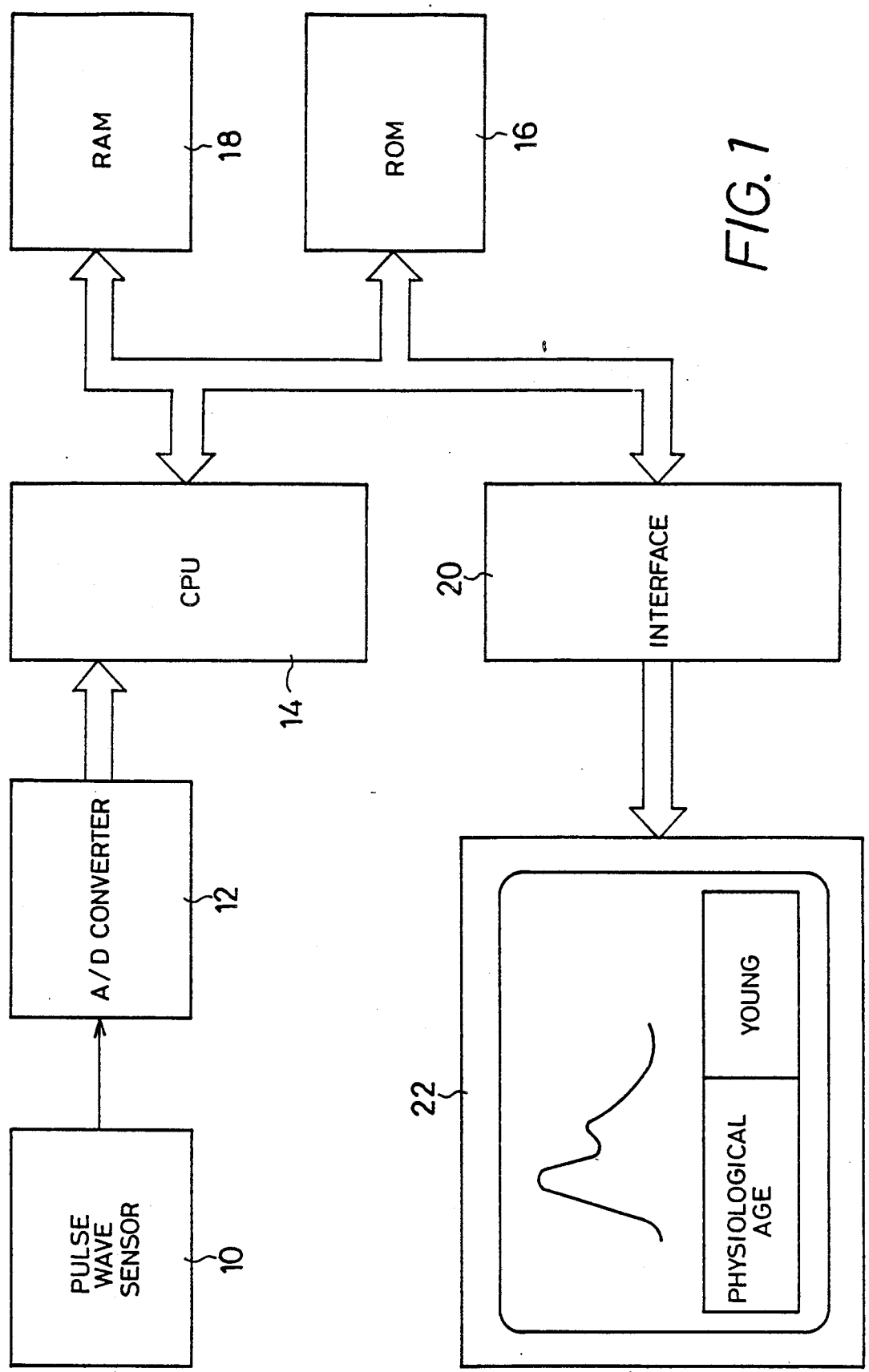
FIG. 1 is a diagrammatic view illustrating the construction of the physiological age measuring apparatus embodying the present invention.
Figure 2A:
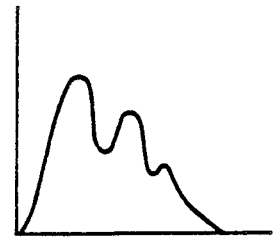
FIG. 2 is a view of four reference waveform models stored in the ROM of the apparatus of FIG. 1, the model (a) corresponding to the infant age group, the model (b) corresponding to the young age group, the model (c) corresponding to the middle age group, and the model (d) corresponding to the old age group.
Figure 2B:
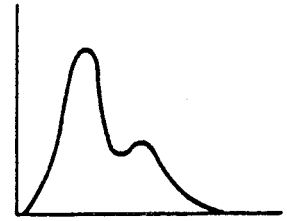
Figure 2C:
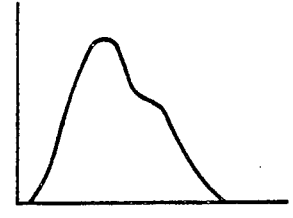
Figure 2D:
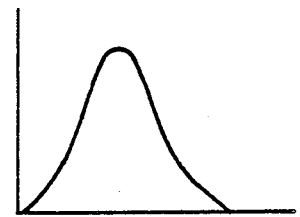

Referring first to FIG. 1 there is shown the physiological age measuring apparatus of the present invention. In the figure reference numeral 10 designates a pulse wave sensor including a pressure sensitive element such as a piezoelectric sheet or a semiconductor strain gauge. The pulse wave sensor 10 is pressed against an arterial vessel (e.g., radial artery) of a subject via body surface, for detecting pulse wave, i.e., oscillatory pressure wave transmitted thereto from the arterial vessel in synchronization with heartbeat of the subject. The pulse wave sensor 10 generates an electric signal SM representing the detected pulse wave, and pulse wave signal SM is supplied to a central processing unit 14 via an analog to digital (A/D) converter 12. The CPU 14 is coupled via data bus to a read only memory (ROM) 16, a random access memory (RAM) 18, and an interface 20. The ROM 16 has four sets of data stored therein which represent four reference waveform models which correspond to four physiological age groups or classes, respectively.

The CPU 16 processes the received signals according to software program pre-stored in the ROM 16 by utilizing a temporary storage function of the RAM 18. In addition, the CPU 14 operates for selecting one of the four reference waveform models stored in the ROM 16, such that the selected waveform model is the most similar to the waveform of the pulse wave sampled through the pulse wave sensor 10, and determining that a physiological age of the subject falls within the age range of the physiological age group corresponding to the selected waveform model. The CPU 14 supplies a display 22 with a display signal representing the selected physiological age group.

In FIG. 2 there are shown the four reference waveform models corresponding to the four physiological groups, namely, infant age group (model (a) in FIG. 2), young age group (model (b)), middle age group (model (c)), and old age group (model (d)). In the present embodiment, the ROM 16 serves as the storing means for storing a plurality of reference waveform models corresponding to a plurality of physiological age groups.

Hereinafter there will be described the operation of the physiological age measuring apparatus constructed as described above.

With the pulse wave sensor 10 pressed against the arterial vessel of the subject via the body surface over the arterial vessel, the control of the CPU 14 begins with step S1 in which pulse wave signal SM supplied from the pulse wave sensor 10 is sampled so that a set of waveform data representing one pulse of the pulse wave is stored in the RAM 18. Step S1 is followed by step S2 in which a correlation coefficient is calculated between the waveform of the sampled pulse and each of the four reference waveform models (a) to (d) stored in the ROM 16, by a known calculation method. Step S2 is followed by step S3 in which one of the four reference models which shows the greatest correlation coefficient of all the models, is selected. In the following step S4 the age range of the group corresponding to the selected waveform model is determined as a physiological age of the subject. Step S4 is followed by step S5 in which the thus determined physiological age of the subject is displayed on the display 22 as shown in FIG. 1. In the present embodiment, a portion of the ROM 16 for storing the software program corresponding to steps S2, S3, S4 of the flow chart of FIG. 3, and the CPU 14 and the RAM 18 for effecting those steps, cooperate with each other to serve as the means for selecting one of the plurality of reference waveform models which is the most similar to the sampled waveform of the subject, and determining a physiological age of the subject based on the age group corresponding to the selected reference waveform model.

As emerges from the foregoing, in the present apparatus, one of the plurality of reference waveform patterns corresponding to the plurality of physiological age groups, is selected such that the selected reference waveform model is the most similar to the sampled waveform of the pulse wave of the subject. The age range of the group corresponding to the selected reference waveform model is determined as a physiological age of the subject, and an indication, e.g., "INFANT", "YOUNG", "MIDDLE" or "OLD", of the thus determined physiological age group is displayed on the display 22. The waveform of pulse wave produced from an arterial vessel of a person, reflects his or her physiological age, and that the waveform is varied primarily by variation in blood output of the heart, and variation in degree of sclerosis of the artery. Thus, it is identified whether or not the subject is physiologically young or old, and by what degree the subject is young or old as compared with normal people.

While in the illustrated embodiment the physiological age groups or classes are displayed with words such as INFANT, YOUNG, MIDDLE or OLD, it is possible to indicate each group in digits. In addition, the plurality of physiological age groups may consist of ten or more age classes. In this case, it is recommended that the display indicate in digits a difference between the measured physiological age of a subject and a real age of the same person.

Although in the illustrated embodiment a single set of the plurality of reference waveform models is used, it is possible to use plural sets each of which consists of a plurality of reference waveform models and which correspond to a plurality of, for example, obesity degrees of subjects, respectively. In this case, first an obesity degree of a subject is determined based on the sampled waveform of pulse wave from the subject, and then one of the plural sets is selected according to the determined obesity degree. A physiological age of the subject is determined using the thus selected set of reference waveform models, similar to the illustrated embodiment wherein a single set of reference waveform models is used.

Figure 3:
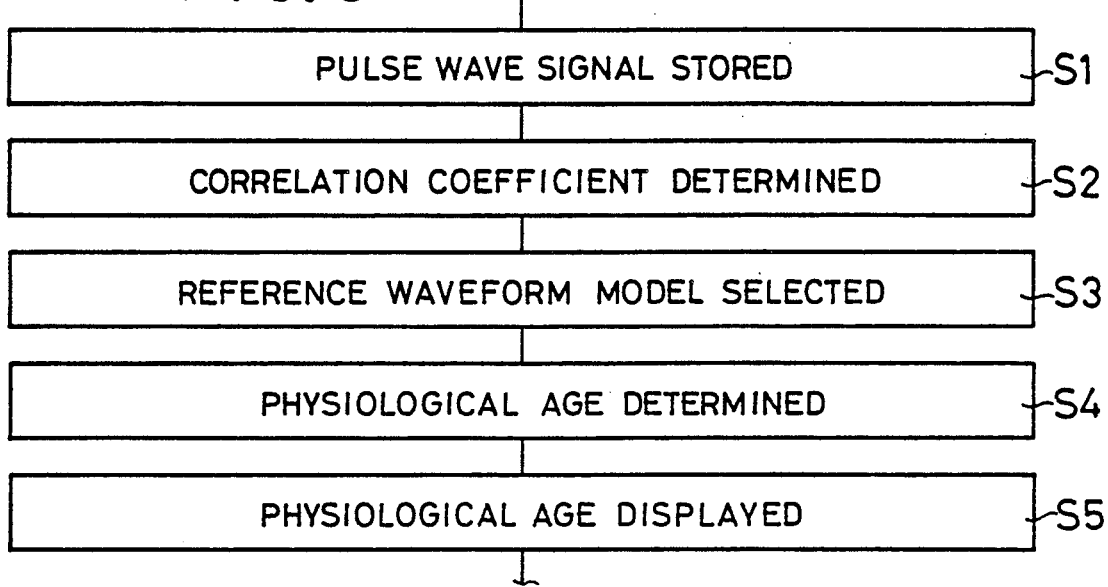
FIG. 3 is a flow chart according to which the apparatus of FIG. 1 is operated.

While in the illustrated embodiment a reference waveform model which shows the greatest correlation coefficient with respect to the sampled waveform of pulse wave of a subject, is selected out of the plurality of reference waveform models at steps S2 and S3 of the flow chart of FIG. 3, it is possible to use a fuzzy inference system for the selection of such a reference waveform model.

While the present invention has been described in its presently preferred embodiment with detailed particularities, it is to be understood that the invention may be embodied with various changes, modifications and improvements that maY occur to those skilled in the art without departing from the spirit and scope of the invention as defined in the appended claims.

What is claimed is:

1. An apparatus for measuring a physiological age of a subject, comprising:
    sampling means for sampling a waveform of a pulse wave produced from an arterial vessel of a subject;
    storing means for storing a plurality of reference waveform models indexed to a plurality of physiological age groups, respectively; and
    determining means for selecting one of said plurality of reference waveform models which is most similar to the sampled waveform of the subject, and determining a physiological age of the subject based on the age group corresponding to the selected reference waveform model.

2. The apparatus as set forth in claim 1, wherein said sampling means comprises a pulse wave sensor which is pressed against said arterial vessel adapted to be so as to detect the pulse wave transmitted thereto from the arterial vessel.

3. The apparatus as set forth in claim 1, wherein said plurality of physiological age groups consist of infant, young, middle and old age groups.

4. The apparatus as set forth in claim 1, wherein said plurality of physiological age groups consist of ten age groups.

5. The apparatus as set forth in claim 1, further comprising display means for displaying the determined physiological age.

6. The apparatus as set forth in claim 1, wherein said determining means selects one of said plurality of reference waveform models which has a greatest correlation coefficient with respect to the sampled waveform of the subject.

* * * * *